United States Patent
Ishmael

(10) Patent No.: US 11,749,386 B2
(45) Date of Patent: Sep. 5, 2023

(54) TECHNOLOGIES FOR GENERATING AND DEPLOYING ENCRYPTED CODES DESIGNED TO AUTO-CONFIGURE EVENTS AND EXECUTABLE ACTIONS ON USER DEVICES

(71) Applicant: Olusegun Adekunle Ishmael, Chicago, IL (US)

(72) Inventor: Olusegun Adekunle Ishmael, Chicago, IL (US)

( * ) Notice: Subject to any disclaimer, the term of this patent is extended or adjusted under 35 U.S.C. 154(b) by 795 days.

(21) Appl. No.: 16/606,437

(22) PCT Filed: Apr. 18, 2018

(86) PCT No.: PCT/US2018/028122
§ 371 (c)(1),
(2) Date: Oct. 18, 2019

(87) PCT Pub. No.: WO2018/195171
PCT Pub. Date: Oct. 25, 2018

(65) Prior Publication Data
US 2020/0402622 A1 Dec. 24, 2020

Related U.S. Application Data

(60) Provisional application No. 62/487,846, filed on Apr. 20, 2017.

(51) Int. Cl.
*G16H 10/60* (2018.01)
*G16H 40/67* (2018.01)
(Continued)

(52) U.S. Cl.
CPC .......... *G16H 10/60* (2018.01); *G06Q 10/109* (2013.01); *G16H 20/10* (2018.01); *G16H 40/20* (2018.01);
(Continued)

(58) Field of Classification Search
CPC ........ G16H 20/10; G16H 10/60; G16H 40/67; G16H 40/20
See application file for complete search history.

(56) References Cited

U.S. PATENT DOCUMENTS

| | | | | |
|---|---|---|---|---|
| 9,529,969 | B2 * | 12/2016 | Brennan | G02B 7/1815 |
| 2009/0029724 | A1 * | 1/2009 | Hardy | G06Q 10/109 |
| | | | | 455/466 |

(Continued)

*Primary Examiner* — Mark Holcomb
(74) *Attorney, Agent, or Firm* — Polsinelli PC

(57) ABSTRACT

In some examples, a system obtains respective information about users and, based on the respective information, generates respective events including an action and parameters defining a trigger for the action. For each user, the system generates a code with data corresponding to a respective event and information, the data including executable data for configuring the respective event and parameters in one or more applications. The system transmits the code to a device associated with the user, which when processed at the device, cause the respective event and parameters to be configured in an application on the device and the trigger to activate the application or device to perform the action, including transmitting, to the system or a display, an indication of a status of the respective event and/or action. The system can also receive an indication when the event has occurred or the trigger has been satisfied.

20 Claims, 8 Drawing Sheets

(51) Int. Cl.
*H04W 12/77* (2021.01)
*G06Q 10/109* (2023.01)
*H04L 67/55* (2022.01)
*G16H 20/10* (2018.01)
*G16H 40/20* (2018.01)

(52) U.S. Cl.
CPC ............. *G16H 40/67* (2018.01); *H04L 67/55* (2022.05); *H04W 12/77* (2021.01)

(56) References Cited

U.S. PATENT DOCUMENTS

| | | |
|---|---|---|
| 2010/0324936 A1 | 12/2010 | Vishnubhatla et al. |
| 2013/0317753 A1 | 11/2013 | Kamen |
| 2014/0250184 A1 | 9/2014 | Brown et al. |
| 2014/0278548 A1* | 9/2014 | Munro .................. H04W 12/02 705/3 |

* cited by examiner

TECHNOLOGIES FOR GENERATING AND DEPLOYING ENCRYPTED CODES DESIGNED TO AUTO-CONFIGURE EVENTS AND EXECUTABLE ACTIONS ON USER DEVICES

CROSS-REFERENCE TO RELATED APPLICATIONS

This application claims the benefit of, and priority to, U.S. Provisional Patent Application No. 62/487,846, filed on Apr. 20, 2017, entitled "SYSTEMS AND METHODS FOR GENERATING CLIENT DEVICE REMINDERS", which is hereby expressly incorporated by reference in its entirety.

BACKGROUND

Quality healthcare outcomes depend upon patients' adherence to recommended treatment regimens. For example, in some disease conditions, more than 40% of patients sustain detrimental outcomes by misunderstanding, forgetting, or ignoring healthcare instructions. Noncompliance is a major factor in the increasing healthcare costs in the United States. Patients' noncompliance with medical direction costs the U.S. healthcare system approximately $289 billion annually. Managing and ensuring compliance of medical treatment regimens is particularly challenging as medical treatment regimens often involve time-sensitive information and tasks, and related treatment and medical data is typically scattered across various locations and difficult to integrate with the numerous, and increasingly distinct, devices and applications available to users.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict various aspects of the present disclosure but are not to be considered limiting in scope.

DETAILED DESCRIPTION

Figure 1:
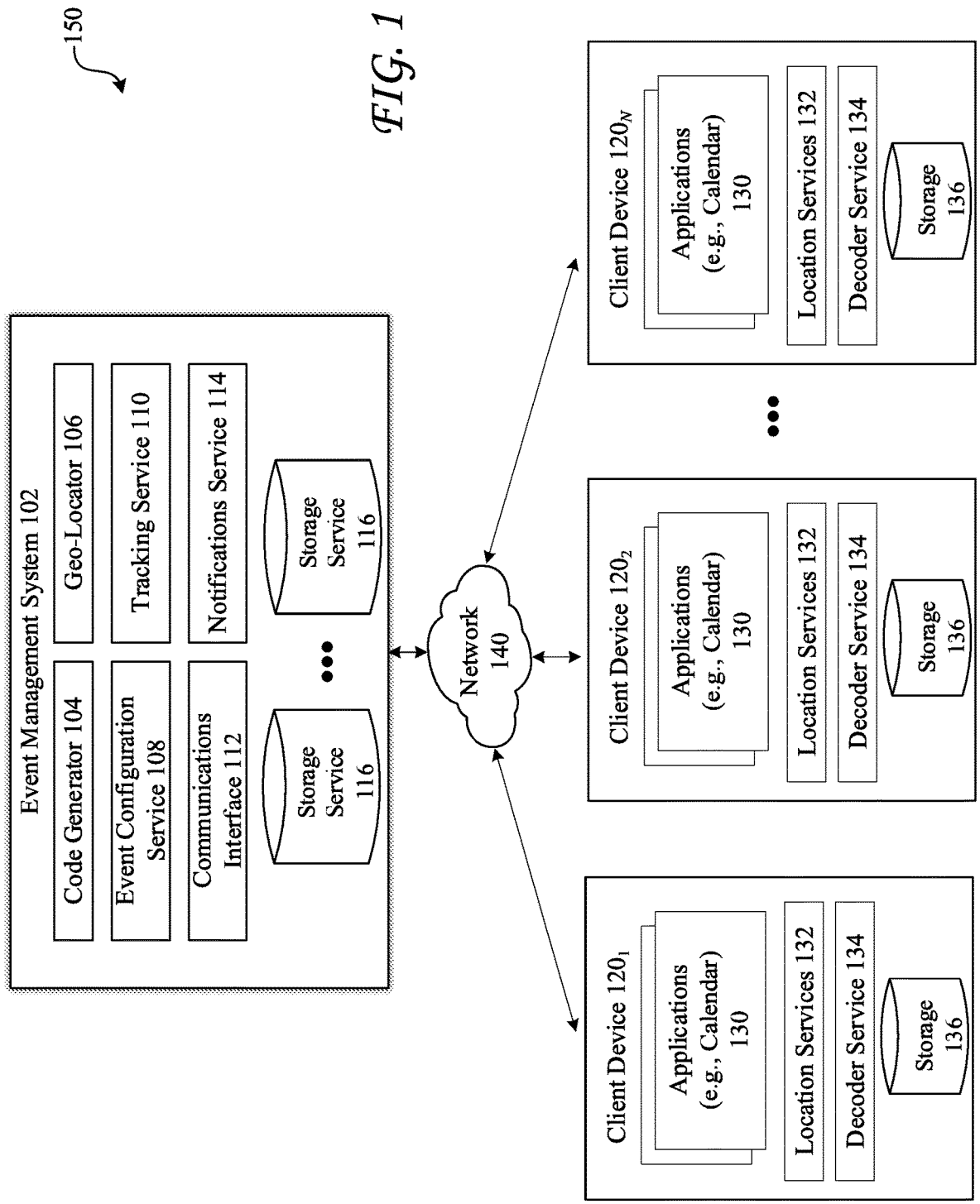
FIG. 1 is a block diagram of an example distributed computing environment for distributing respective encrypted codes to client devices over a network, according to some embodiments.

Aspects of the present disclosure involve systems and methods for generating and distributing encrypted codes with encoded executable data capable of interacting with specific client applications and devices and configuring user-specific events programmed to communicate event-based, location-based, and/or time sensitive information based on encoded parameters. The encrypted codes can be customized for users and distributed to user devices over a network, in order to deploy the user-specific events on the user devices and auto-configure the user devices to monitor the events and communicate related information, such as time-sensitive and/or location-based alerts, upon detecting a triggering condition. The encoded data and events in the encrypted codes can be designed to integrate with one or more specific client applications, such as calendar or map applications, and/or access device resources to communicate alerts and time-sensitive or location-sensitive information to users and any other desired recipients.

The approaches herein can address specific technical challenges in various contexts, such as configuring private and/or time sensitive events, operations, and information in a distributed environment. For example, in a medical context, medical information has strict privacy/security requirements and medical events (e.g., treatments, medication regiments, tests, procedures, etc.) are typically individualized and have time sensitive requirements. In this example, the approaches herein can generate and distribute to specific user devices codes containing encrypted, user-specific medical information and events and encoded executable data (e.g., software code or instructions) capable of automatically deploying the user-specific events at the user devices and using hardware resources and client applications at the user devices to monitor the events and event parameters (e.g., triggers, rules, conditions, etc.) and communicate time-sensitive medical information to specific users and devices.

In some examples, the disclosed technology can provide and/or generate event indications and corresponding reminders that may be automatically populated within, and/or injected into, an application, such as a calendar application on a mobile device, based on an encrypted code deployed at the mobile device. Said reminder can be triggered based one or more triggering parameters configured through the encrypted code, such as geographic location parameters, date and time parameters, network connectivity or availability of a secondary device, user activity, etc. In various aspects, a server computing device may generate an encrypted scannable code, such as a barcode, iQR/QR code, or an alphanumeric code, that can be inputted into an application on a user's device, embedding an event or action for the user.

For example, in the health care realm, the encrypted code can auto-configure an event on a client application of the user's device, and logic or data for generating a reminder. The event may correspond to events associated with medication regimens (e.g., time schedules for consuming medication), health maintenance screening tests, medical procedures, medical treatment regimens, and/or the like, and the event can be configured to trigger a reminder at a predefined date/time and/or upon a specific activity or condition, such as when the user is within a predefined radius of a testing facility. The generated code is scanned and/or decoded by a client device associated with the user, and the scanned or decoded code can subsequently auto-populate an event defined in the code into a calendar application at the client device. The code can also access a geolocator functionality of the client device, as well as other resources or functionalities at the client device, such as imaging, communication, display, and audio functionalities. Once the event is configured in the calendar application and/or the geolocator application, a reminder can be triggered and communicated to the user and/or any device(s) in compliance with time-sensitive, data, and/or privacy requirements.

Although the present application uses the health care industry as examples to illustrate the inventive concepts described herein, it is contemplated that aspects of the present disclosure may be applied to other industries and fields, such as networking and computing events, educational settings, retail, sporting events, theater events, troubleshooting events, etc.

FIG. 1 is a block diagram of an example distributed network environment 150 for distributing respective encrypted codes and auto-configure events and parameters at client devices, in accordance with various aspects of the present disclosure. As illustrated, the computing network environment 150 includes an event management system 102 that can configure events and generate and distribute encrypted codes (alphanumeric, barcodes, iQR or QR) to client devices $120_1$, $120_2$, $120_3$ (collectively "120" hereinafter). The encrypted codes are embedded with user and event information, such as medical information, medical events, and event parameters (e.g., triggers, conditions, rules, etc.), which may be processed by the client devices 120 to inject events into specific client applications (e.g., a calendar application, a geolocator application, etc.) on the client devices 120 and manage event-related communications, such as reminders or alerts, based on event parameters defined in the encrypted codes.

The event management system 102 may include a code generator 104 to generate the encrypted codes (alphanumeric, barcodes, QR) for specific users or client devices 120. The code generator 104 may generate a machine-readable optical label that contains information corresponding to a user (e.g., medical information corresponding to a patient) and/or events corresponding to the user, such as medical events. The encrypted codes may contain logic and/or parameters for triggering actions, such as reminders or alerts, interacting with client applications 130 and using client resources, such as location services 132, storage 136, sensors (e.g., image sensors, motion sensors, noise sensors, impact sensors, etc.), processors, etc.

The encrypted codes can be distributed via network 140, which can include one or more private and/or public networks. In some cases, the encrypted codes may be distributed or obtained at pharmacies on users obtaining prescriptions. For example, the encrypted codes can be provided on a user's prescription information sheet or on a medication bottle that has the encrypted code on the label. In other examples, the encrypted codes can be distributed or obtained from physician offices, emergency rooms (e.g., via discharge documents), insurance companies (e.g., via insurance documents or electronic messages). The encrypted codes can auto-configure events and electronic communications (e.g., reminders or alerts) to ensure user compliance with time-sensitive health maintenance procedures, tests evaluations, etc.

The event management system 102 can store user and/or event information in storage 116, and use the user and/or event information to configure events through an event configuration service 108. The event configuration service 108 can analyze and/or identify relevant information in storage 116 and configure events and event-related information, such as event parameters, which can be used by the code generator 104 to generate the encrypted codes.

The storage service 116 can store any information necessary for generating or configuring events. For example, the storage service 116 can store medical information to configure medical events for users. Such medical information may include standard medical and clinical data gathered in a health care setting, comprehensive patient history data, etc.

The event management system 102 can also include a geo-locator service 106 to calculate, identify or track location information about the client devices 120, users, event conditions, etc. The event management system 102 can also include a tracking service 110 that tracks when an activity or event has been performed or completed, or when a notification associated with an event or activity has been received from the client devices 120. The event management system 102 can also include a notifications service 114 to communicate notifications to the client devices 120 and/or other users/devices. For example, if an activity, task, or event has not been performed or completed by a user, as determined based on the tracking service 110, the notifications service 114 can generate a notification indicating that the activity, task, or event has not been performed or completed or requesting confirmation that the activity, task, or event has indeed been performed or completed.

Users may interact with events via the client devices 120. The client devices 120 can include, without limitation, smart phones, laptops, tablet computers, smart wearable devices, gaming systems, smart televisions, IoT (Internet of Things) devices, etc. The client devices 120 include a decoder service 134 configured to receive and process (e.g., decode, translate, convert, etc.) encrypted codes from the event management system 102. In some cases, the client devices 120 can scan the encrypted codes using a dedicated scanner (not shown) and extract data encoded in the scanned, encrypted codes via the decoder service 134. As previously mentioned, the data encoded in the encrypted codes can include user information (e.g., medical information), device information (e.g., application information, hardware information, addressing information, etc.), event information (e.g., event details, parameters, etc.), etc.

The client devices 120 may be any processing devices capable of implementing and/or executing processes, software, applications, wired and/or wireless communication technologies (e.g., Ethernet, Bluetooth, Wi-Fi, cellular, etc.), etc., and operating computing resources such as network interfaces and/or transceivers (e.g., Bluetooth, Wi-Fi, cellular, etc.), storage resources, sensors, processors, etc. In some cases, the client devices 120 include network-enabled devices and/or software, such as a calendar and a geolocator application (e.g., location services 132) configured to communicate over the communications network 140 (e.g., browsing the internet). The client devices 120 may include one or more processors that process software or other machine-readable instructions and may include a storage 136 (e.g., memory) to store the software or other machine-readable instructions and data, such as the encrypted codes and/or decoded data from the encrypted codes. The one or more processors can enable the client devices 120 to transmit information over the network 140 to event management system 102 and/or a database enabled to accept completion or non-completion of triggered activity or event (e.g., storage service 116). For example, the client devices 120 can detect that they are located within a predetermined radius of a physical location and trigger an event/activity reminder based on such location information. Alternatively, in the case of a Bluetooth enabled container, the generated reminder is marked as completed on the opening and closure of said container.

In some cases, the client devices 120 include a dedicated scanner for reading specific barcodes, decoding specific iQR or QR codes, etc., and a decoder (e.g., decoder service 134) for decoding the codes (e.g. alphanumeric codes, barcodes, iQR or QR codes), and one or more software applications 130 (e.g., client-side software) for processing these codes and/or associated information and auto-populating calendars with events and/or calendar reminder indications, tracking events on the calendar, sending reminders and/or triggering alarms, etc. In some cases, the codes can access the location services 132 on the client devices 120 and may connect the calendar event to a geolocator application associated with the location services 132. Thus, the client devices 120 can scan and decode an encrypted code to obtain the embedded information and events and automatically inject or configure the information and/or events into the calendar and/or geolocator applications.

During the initial setup at the client devices 120, which is pushed by decoding the supplied code, the user can be asked for access to the specific applications 130 and services 132 (e.g., calendar and/or geolocator application or service), where the user may choose a singular or general authorization. Singular authorization is for a one-time event that will expire once the event/activity (e.g., a recommended dosage or treatment) has been completed. Once complete, the user may need to re-grant access for each new event or activity (e.g., dosage or treatment). A general authorization will allow for access to one or more of the user's applications 130 (e.g., calendar) for multiple events. As long as the user remains with the authorized application, any and all events, medical or otherwise, will be populated or configured into the application (e.g., calendar) with the necessary reminders and alarms. The encrypted codes can include executable data, including executable code for creating actions in the applications 130 on the client devices 120 associated with the data types used by the encrypted codes. The executable code can include instructions for interacting with applications 130 and/or resources on the client devices 120, instructions for formatting data or events for specific devices or applications, etc. The event information in the encrypted codes can include parameters defining when to generate an action (e.g., reminder, alert, etc.), how to generate a message (e.g., reminder or alert), where to send or display the message (e.g., display on the user's device, event management system 102, etc.), etc. To this end, the parameters can define network addressing information for transmitting triggered communications (e.g., an IP address of the event management system 102, an IP address of a user device, etc.), application and/or resource identifiers for interacting with the application and/or resources (e.g., API calls), protocol information for transmitting messages, formatting information, etc.

Once an activity/event has been injected or configured into a client device and/or client application (e.g., calendar), a user may interact (within the parameters set for the activity/event) with any reminders or alerts generated for the activity/event, to obtain relevant information corresponding to the information and/or corresponding event embedded in the code. For example, if the encrypted code includes medical information involving dosage information, how to use a medication and duration (e.g., a medication regimen), etc.; the reminder may provide information defining a direction of use for the medication, the number of doses (e.g. inventory), side effects, when a refill is needed, prescribing doctor information, contact information, and/or the like.

In some embodiments, the client devices 120 may receive an indication that respective events contained in the reminders have been completed. The completion can be transmitted to the event management system 102, which can track the reminders and/or completion via the tracking service 110 and/or store such data in via the storage service 116. For example and with reference to the medication example above, a calendar application of a client device may be automatically updated to show that the event has passed and the medication was taken or a refill is needed/obtained, and an indication of such may be transmitted to the event management system 102. In the event that one or more client devices 120 do not receive the user feedback or indication, the one or more client devices 120 may provide a notification to the event management system 102 indicating a lack of compliance, which in turn will trigger a notification to the originator of the reminder and other predefined person/s.

In some configurations, the information transmitted by the client devices 120 back to the event management system 102 (e.g., reminders, notifications, indication of event/task completion, indication of event/task lack of completion, etc.) can be encrypted via one or more encryption schemes/algorithms (e.g., symmetric key/private key schemes, public key schemes, etc.). Moreover, in some cases, the event management system 102 can perform a cyclic redundancy check or checksum, such as a hash algorithm/function (e.g., SHA-x, MD5, fingerprint function, etc.), to verify the authenticity of the received information, detect errors in the received information, check the overall data integrity, etc.

In some configurations, some or all of the information transmitted by the client devices 120 back to the event management system 102 can be transmitted in plaintext. For example, in some cases, when sending information to the event management system 102, the client devices 120 may encrypt some of the information (e.g., private information such as medical information, user private information, financial information, personal data, etc.) and send other portions of information in plaintext. The client devices 120 may determine what portions (if any) of the information sent to the event management system 102 to encrypt based on one or more factors, such as user preferences, network security conditions (e.g., whether the information is being transmitted via a public network, such as the Internet, or a secure/private network, such as a virtual private network or a local area network), rules or preferences specified by the event management system 102, the type of information being transmitted (e.g., sensitive or personal information vs. public information, the computing device and/or network protocol used to transmit the information, risk assessment information, governing policies or guidelines (e.g., Health Insurance Portability and Accountability Act), the capabilities of the client device transmitting the information to the event management system 102, etc.

The location services 132 can include a geolocation application or unit which may be used to track event parameters (e.g., location parameters) and generate automatic reminders indicative of the event or action defined in the encrypted code based on the location of the client devices 120. For example, assuming the client devices 120 are smart phones, the location services 132 may track the location of the smart phones and trigger a reminder based on the location of the smart phone, such as if/when the smartphone is near or at a target location defined by one or more event parameters in the respective encrypted codes. The location services 132 may automatically establish a target location for a reminder of an event or action. Example of target locations may include any defined physical location, such as a location for a pharmacy (when a medication refill is due), testing facility (when a specific test is due or is required), medical facility, residence, commercial office, etc. The location services 132 may facilitate a location-based reminder when a current location matches the target location. The current location may be determined via GPS (global positioning system), cellular triangulation, radar sensing data, or other location identifying techniques. In addition to providing location-based reminders, the location services 132 capabilities can be combined with other capabilities, such as date and time services, to generate reminders based on a combination of triggers, such as a location, a date and time, an activity (e.g., user interaction with a device), or any combination.

Figure 2:
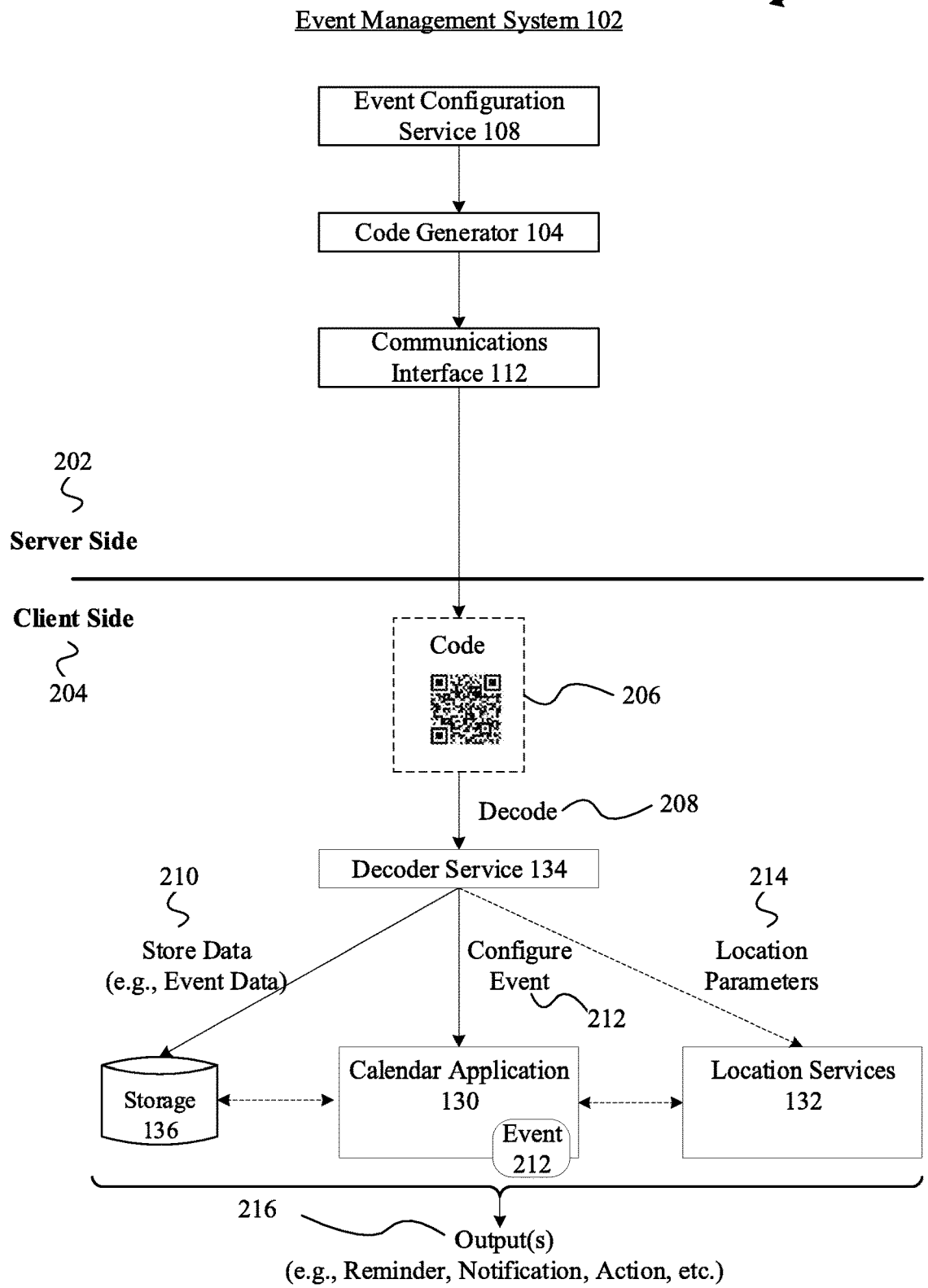
FIG. 2 is a block diagram of an example process for distributing and processing respective encrypted codes with encoded event data in the example distributed computing environment illustrated in FIG. 1.

FIG. 2 is a block diagram of an example process 200 for distributing and processing respective encrypted codes with encoded event data in a distributed computing environment, such as distributed computing environment 150 illustrated in FIG. 1. In this example, at the server side (202), the event configuration service 108 on the event management system 102 can configure an event and event parameters based on event-related information, which can be obtained from the storage service 116. The code generator 104 can then generate an encrypted code based on the configured event.

The encrypted code can encode data associated with the event and/or the user, time and/or date information associated with the event, event requirements, event exceptions, location information associated with the event (e.g., a geolocation for the event), tasks or activities associated with the event (e.g., take a medication, perform a test, etc.), addressing information for communicating event information (e.g., a network address associated with the event management system 102), formatting guidelines for data associated with the event, application information (e.g., target application for injecting event data and/or configuring the event), resource information, one or more parameters, executable code for configuring the event and performing computing operations (e.g., interacting with client applications and/or resources, monitoring parameters or triggers, signaling data, generating communications, outputting data, generating requests, etc.), and so forth. The one or more parameters can define rules and/or conditions for triggering tasks, communications, actions, etc., associated with the event. For example, the one or more parameters can define triggers for the event, such as a date and/or time (or range) for the event, a location(s) for the event, a precursor activity or condition for the event, etc.

When the triggers defined for the event by the one or more parameters occur, the executable code in the encrypted code and/or the client device/application configured with the event can generate the task, communication (e.g., alert, reminder, notification), action, etc., defined in the encrypted code. For example, if the one or more parameters define a triggering time for taking a medication, the client device or calendar can generate a reminder at the triggering time, which can indicate to the user that it is time to take the medication. In some cases, prior to generating the reminder, the client device or calendar can first verify that a reminder has not already been generated/sent for the triggering time or that the user has not already taken the medication. For example, the client device can search a stored log of reminders to verify that the current reminder has not already been sent, and check whether a prescription container has already been opened at the schedule time.

Once the code generator 104 has generated the encrypted code 206, the event management system 102 can send the encrypted code 206 to client device $120_1$ via the communications interface 112. At the client side (204), the client device $120_1$ can receive the encrypted code 206 and decode 208 the encrypted code 206 via the decoder service 134. Here, the client device $120_1$ can extract any data encoded in the encrypted code 206, including user information, device information, network information, event information, event parameters, executable code, etc. The client device $120_1$ can then store at least a portion of the extracted data 210 in storage 136, and configure the event 212 encoded in the encrypted code 206.

In some cases, the client device $120_1$ can configure event 212 in calendar application 130. For example, the client device $120_1$ can interact with calendar application 130, create the event 212 in the calendar application 130, inject any event data into the event 212 created on the calendar application 130, and configure one or more reminders for the event 212 on the calendar application 130. The client device $120_1$ can also configure location parameters 214 encoded in the encrypted code 206 for the event 212 for use by the location services 132 to detect when a location of the client device matches the location parameters 214. Such a match between the location parameters 214 and the current (or predicted) location of the client device as determined by the location services 132 can serve as a trigger for the event (or an action associated with the event), an exception for the event, or otherwise inform how the event 212 is managed.

The client device $120_1$ can monitor any triggers defined by the one or more parameters in the encrypted code 206, such as rules, conditions, activities, etc., defined as triggers, prerequisites or precursors for the event or an action associated with the event. In monitoring any triggers defined by the one or more parameters, the client device $120_1$ can interact with or monitor resources at the device, such as calendar application 130, location services 132, storage 136, one or more sensors, and/or any other software or hardware resource at the client device. For example, the client device $120_1$ can communicate with hardware and/or software resources at the device to determine the status of the device, the location of the device, the current time, a current state or context of the user and/or device, surrounding conditions (e.g., environmental conditions, nearby objects, nearby activity, etc.), and/or any other information that is pertinent to the event 212 as defined by the one or more parameters or encoded data in the encrypted code 206. The information obtained by the client device $120_1$ from the hardware and/or software resources can be considered as part of a determination of whether a trigger(s) for the event 212 and/or an associated event-action (e.g., a reminder) has occurred.

When the client device $120_1$ detects that a trigger has occurred or a triggering condition has been satisfied, the client device $120_1$ can generate output 216 for the event 212. The output 216 can be a reminder, a notification, an alert, an action (e.g., a command, an application or service call, an error, an electronic communication, etc.). For example, the output 216 can be a reminder transmitted to a display informing the user of the event 212 or a pending task associated with the event 212. As another example, the output 216 can be an API call to a pharmacy or doctor prescription database or system indicating that a refill of a prescription is needed.

In some cases, the output 216 from the client side 204 can be communicated via a network (e.g., 140) to event management system 102 and/or any other device or entity. The output 216 can be transmitted over the network in plaintext or encrypted via one or more encryption schemes/algorithms, as previously explained with reference to FIG. 1.

Figure 3:
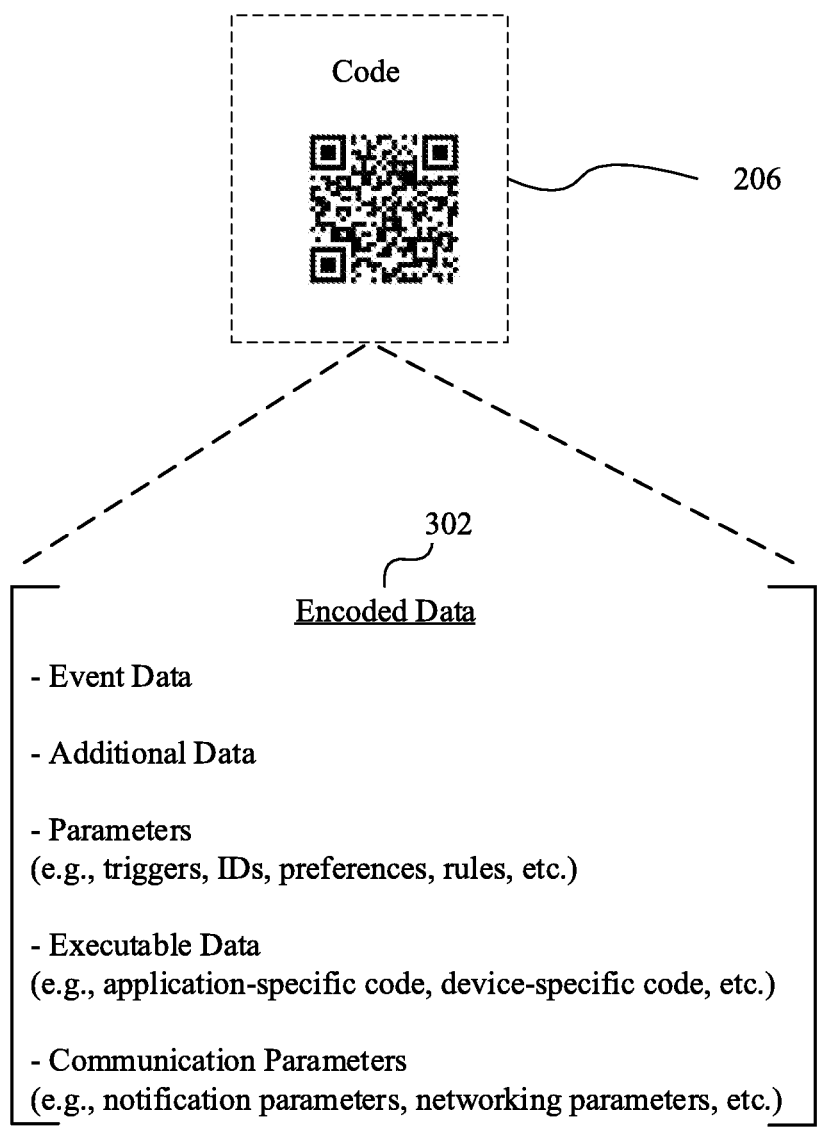
FIG. 3 illustrates an example configuration of an encrypted code with encoded event data and executable code for installing or configuring an event and event parameters on a client device.

FIG. 3 illustrates an example configuration of encrypted code 206. In this example, the encrypted code 206 contains encoded data 302 defining a particular event for a particular user. The encoded data 302 can be decoded via a decoder (e.g., decoder service 134) as previously described. The encoded data 302 can include event data, such as a description of an event (e.g., take blood pressure, take medication, perform a backup of server data, etc.), and information for the event such as tasks or activities for the event, dependencies, prerequisites, rules, etc. The encoded data 302 can also include additional data relevant to the event or user associated with the event. For example, if the event is a medical event, the additional data can include medical information of the user, instructions for the event, background information, etc. As another example, if the event is a data back event in a network, the additional data can include preferences for the backup, exceptions, etc.

The encoded data 302 can also include one or more parameters. The one or more parameters define triggering conditions, rules, preferences, etc. For example, the one or more parameters can include a first triggering rule providing a date and/or time for generating a reminder associated with the event, a second triggering rule defining location information (e.g., a geolocation, a geofence, a proximity to one or more locations, etc.) for generating the reminder, a third triggering rule defining a prerequisite for generating the reminder (e.g., user opens a prescription container, user fasts for upcoming blood work, etc.), and/or any other triggering rules. The one or more parameters can define priorities for triggers or triggering conditions, and can define any single or combination of triggers for any one event or action.

The encoded data 302 can also include executable data, such as executable code or instructions. The executable data can be executed by one or more processors at the client to perform one or more operations, such as configuring the event at the client device and/or application(s), monitoring parameters or conditions, coordinating communications between hardware and/or software resources, initiating communications or requests, determining whether certain conditions or rules are met, gathering information for the event, formatting data for the event, etc. In some cases, the executable data can include application or device specific code, or instructions for structuring operations, data, and/or communications for specific applications or devices. For example, the executable data can include code for executing operations tailored to the protocol(s), platform, resources, and/or computing environment at the client.

The encoded data 302 can also include communication parameters defining how or where communications generated by the client for the event are to be transmitted. The communication parameters can include network addressing information (e.g., IP address, MAC address, port number, protocol number, etc.) for transmitting event-related communications such as reminders to a specific target device, resource information for routing or providing event-related communications to a display device, etc.

Figure 4:
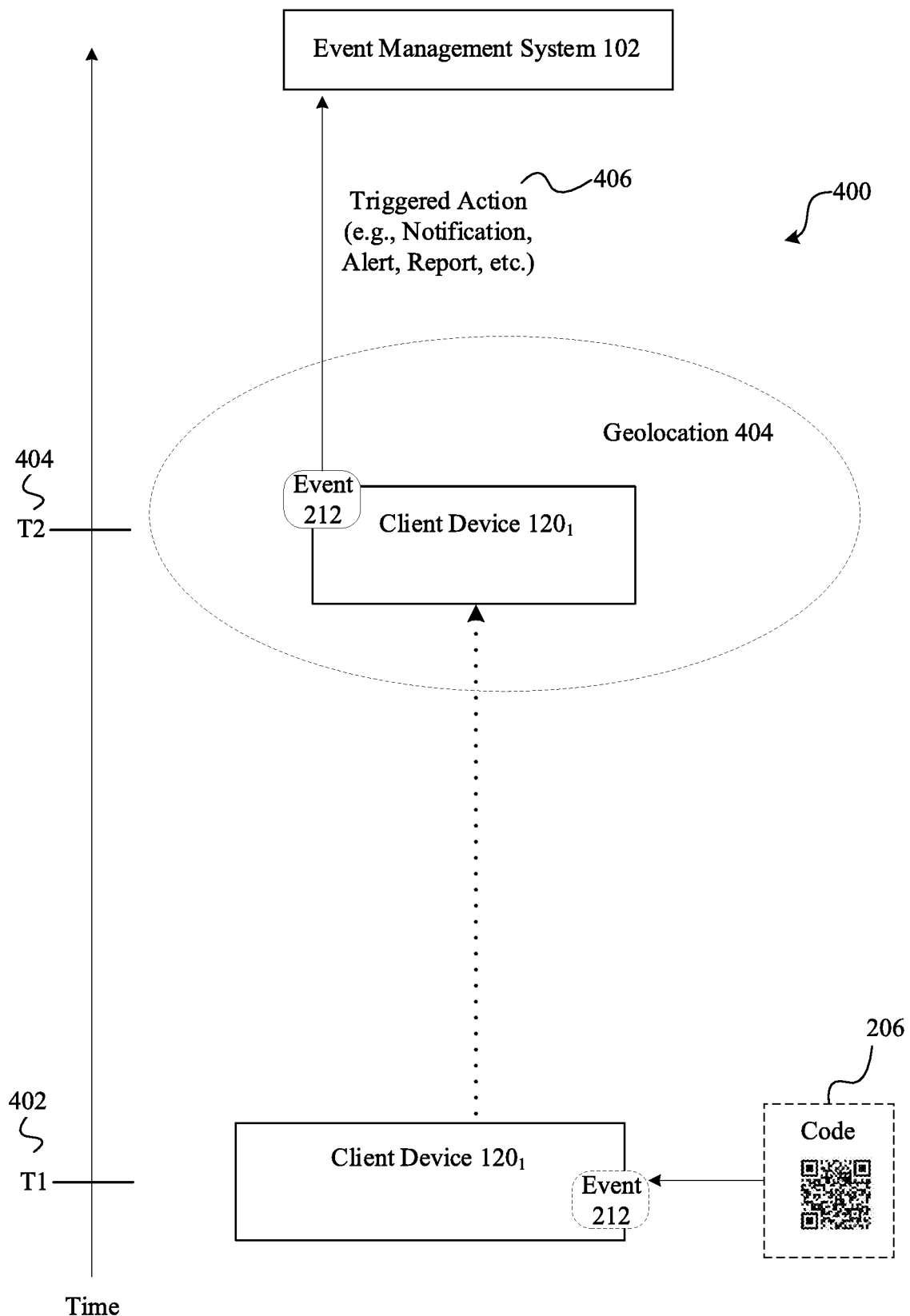
FIG. 4 illustrates an example use case for distributing and processing an encrypted code with encoded data for configuring at a client device an event having location-based triggering parameters.

FIG. 4 illustrates an example use case 400 for distributing and processing an encrypted code 206 with encoded data for configuring at a client device $120_1$ an event having location-based triggering parameters. At time 1 (402), the client device $120_1$ receives and processes the encrypted code 206. The client device $120_1$ configures the event 212 based on the encrypted code 206.

The event 212 in this example includes location parameters defining a geolocation 404 for triggering an action associated with the event 212, such as a reminder. Thus, at time 2 (404), when the client device $120_1$ moves within the geolocation 404, the client device $120_1$ will detect that its location matches the location parameters defining the geolocation 404, and consequently determine that the triggering condition for event 212 has been satisfied. The client device $120_1$ will then generate and transmit the triggered action 406 defined for the event 212. The triggered action 406 can be an alert, a notification, a reminder, an application call, an electronic message, an application output, etc.

Figure 5:
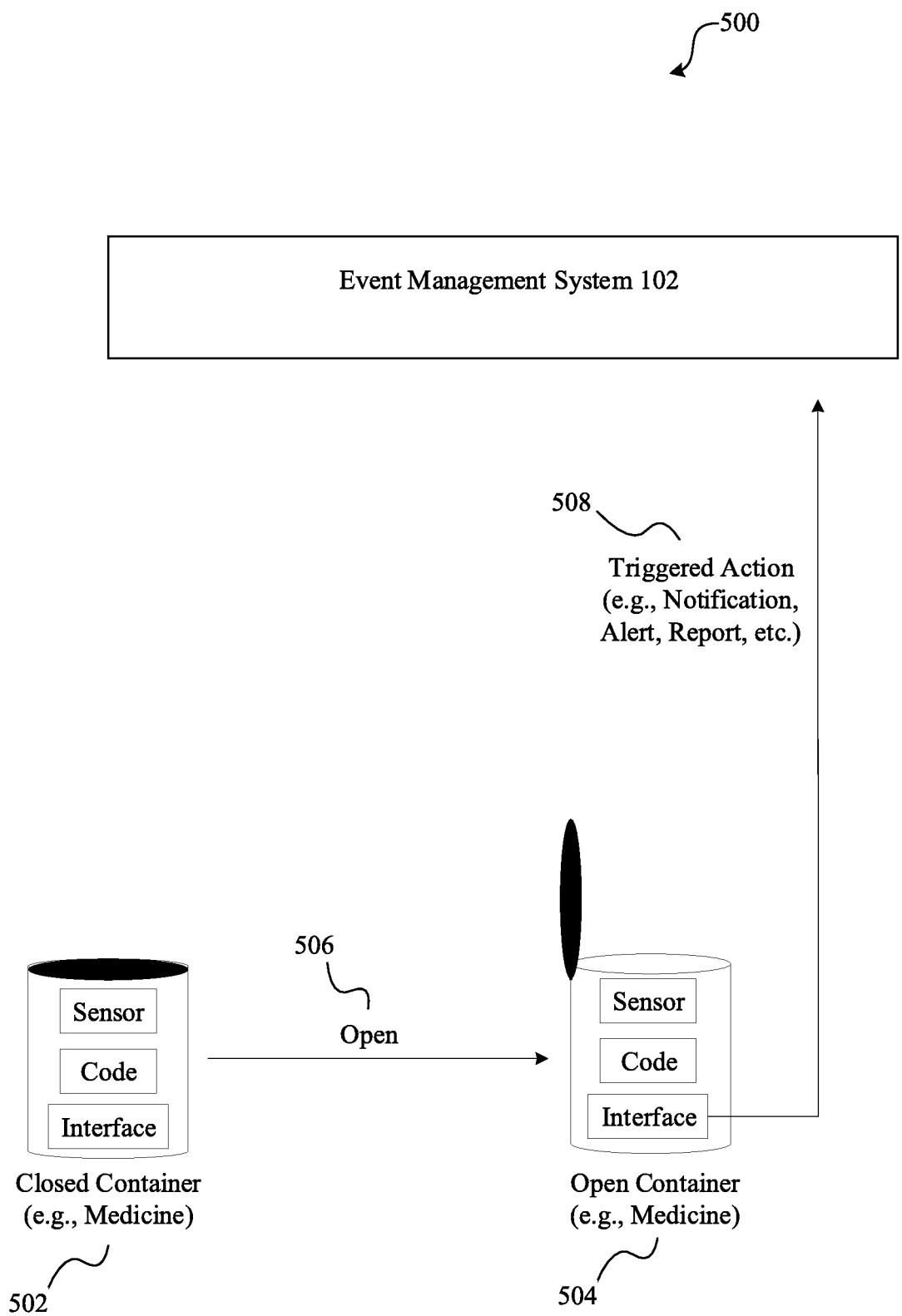
FIG. 5 illustrates an example use case for processing an encrypted code at a container device to configure an event at the container device for transmitting a message from the container device upon sensing an opening of the container device.

FIG. 5 illustrates an example use case 500 for processing an encrypted code 206 at a container device 502 to configure an event at the container device for transmitting a message from the container device upon sensing an opening 506 of the container device. The container device 502 in this example is a closed prescription container. The prescription container includes a sensor for detecting when the container is opened, and code from the encrypted code 206 with instructions for generating a triggered action 508 when the sensor detects that the container is opened.

When the container is opened 506, the opened container 504 will generate the triggered action 508, which in this example is a message (e.g., notification, alert, report) to event management system 102 indicating that the container was opened. Based on a determination that the container was opened, the event management system 102 can infer that the user has taken the medication in the container as instructed by the event configured for the encrypted code 206. If alternatively, the container is not opened within a predefined range of time defined for the event, or the sensor of the container does not detect the opening 506 of the container, the code can instead trigger a reminder to be displayed to the user via a display device, communicated to the user at a device or electronic target, and/or communicated to the event management system 102. The container can include an interface (e.g., communications interface) for displaying information and/or transmitting electronic communications.

Figure 6:
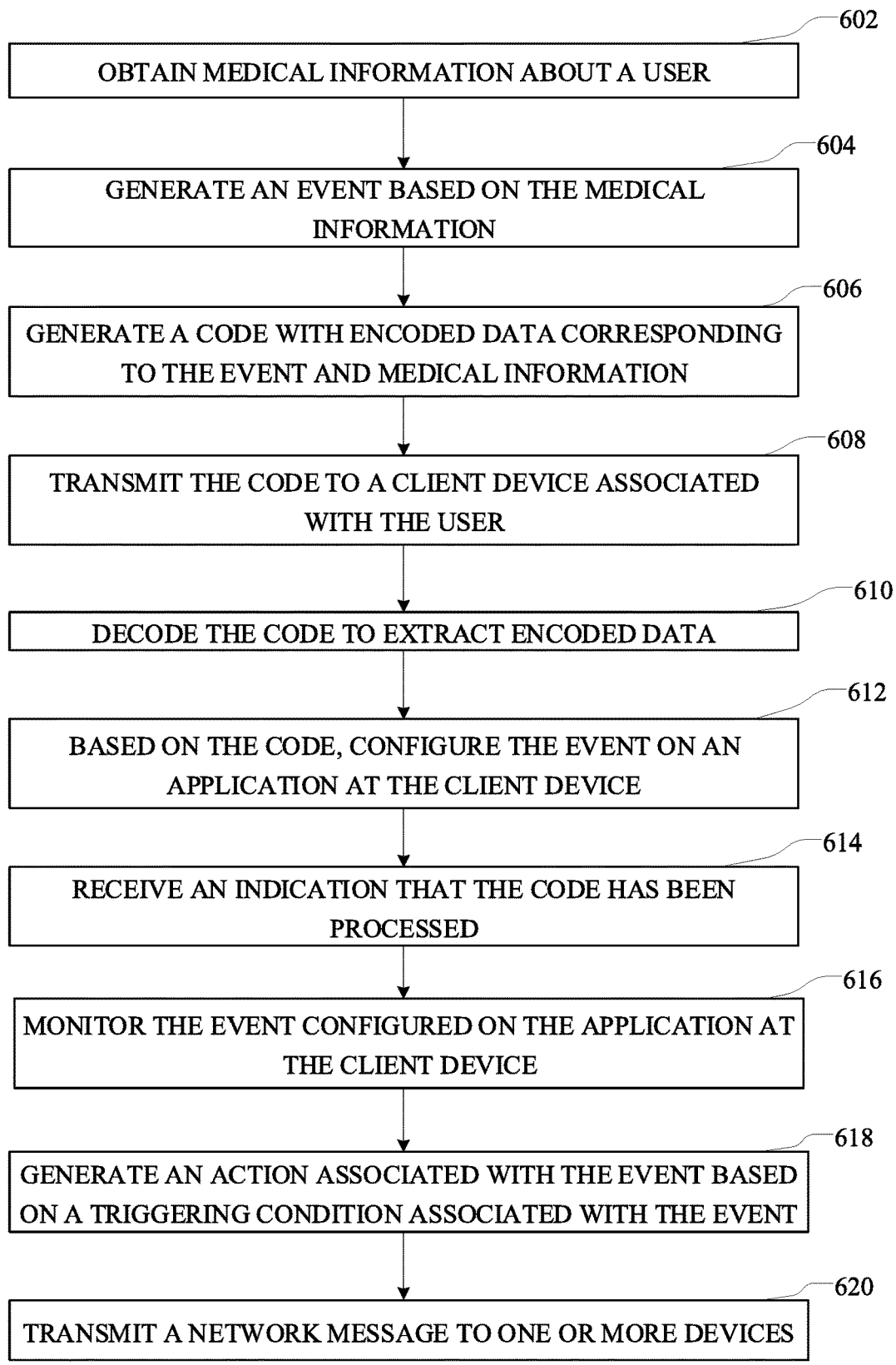
FIG. 6 is a flowchart illustrating an example process for generating and distributing encrypted codes to client devices over a network and processing the encrypted codes for auto-configuring respective events and event parameters in respective applications at the client devices, according to some embodiments.
Figure 7:
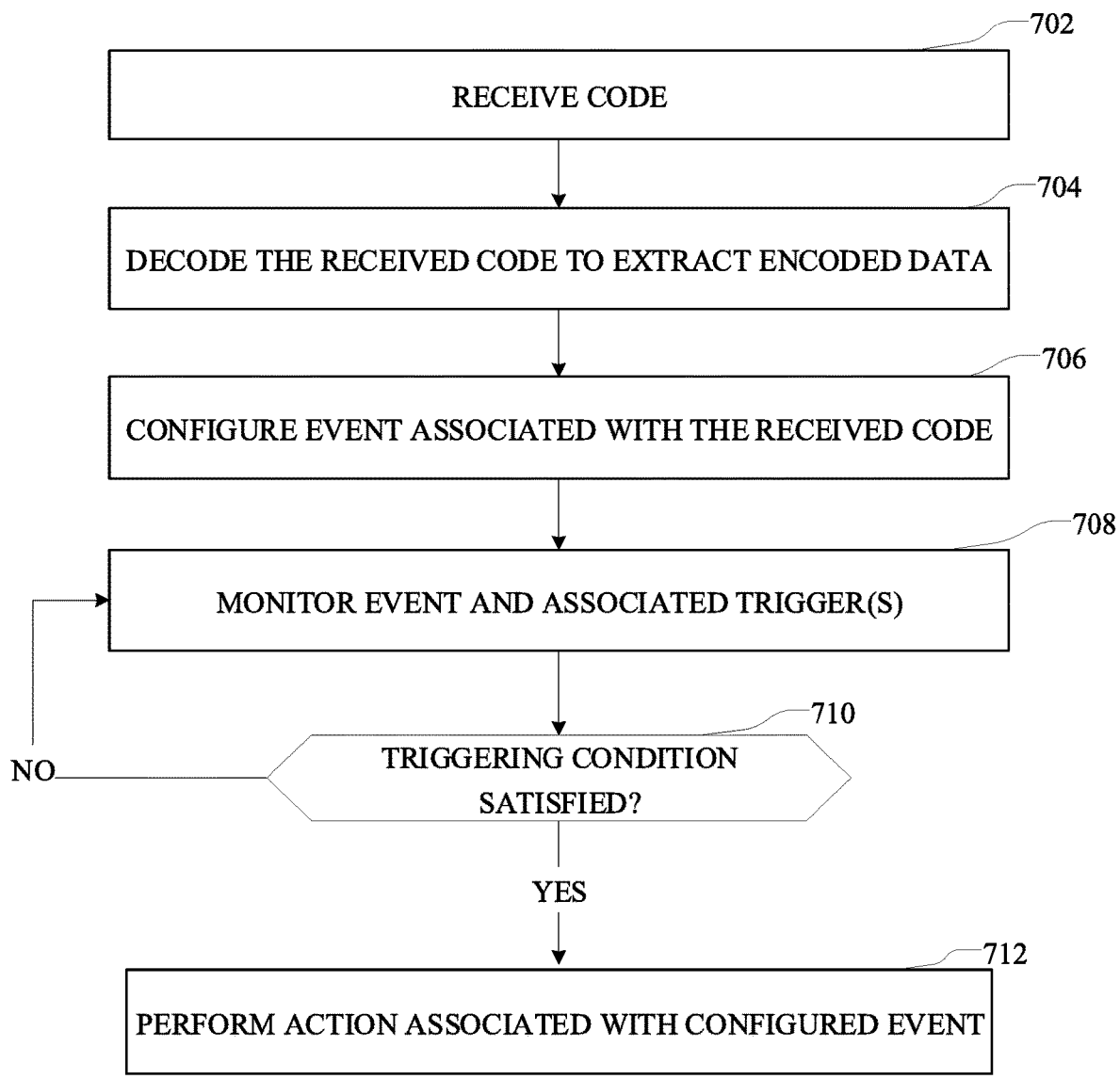
FIG. 7 is a flowchart illustrating an example process for processing an encrypted code, configuring an event encoded in the encrypted code, and performing an action associated with the event upon detecting a trigger defined for the event, according to some embodiments.

Having disclosed example system components and concepts, the disclosure now turns to the example methods shown in FIGS. 6 and 7. For the sake of clarity, the methods are described with reference to the event management system 102 and one or more client devices 120, as shown in FIG. 1, configured to perform the various steps or operations in the method. The steps outlined herein are examples and can be implemented in any combination thereof, including combinations that exclude, add, or modify certain steps.

FIG. 6 depicts an example method 600 for generating and distributing encrypted codes (e.g., 206) to client devices (e.g., 120) over a network (e.g., 140) and processing the encrypted codes for auto-configuring respective events and event parameters in respective applications at the client devices.

For explanation purposes and the sake of clarity, the steps 602-620 and/or concepts below are described with reference to event management system 102 and an example client device (e.g., $120_1$) in the distributed network environment 150, though it should be noted that in many cases, the steps 602-620 and/or concepts below can be implemented between the event management system 102 and multiple client devices 120. For example, the encrypted codes can be distributed to, and processed by, a single client device in some cases, and distributed to, and processed by, multiple client devices in other cases. In examples where the encrypted codes are distributed to, and processed by, multiple client devices, the encrypted codes can be customized to specific client devices and/or associated users such that the data, functionality, and experience can vary for different client devices and/or users.

Moreover, for the sake of clarity and explanation purposes, the methods 600 and 700 in FIGS. 6 and 7 are described in the medical context with reference to medical events, parameters and actions associated with the medical events, and users associated with the medical events. However, it should be understood that the methods 600 and 700, and associated concepts, can be implemented in other contexts and/or configurations, involving events, parameters, users, devices, information, etc., outside of the medical context, which are contemplated herein, such as, without limitation, networking or computing events in a networking and/or computing context, educational events in an education context, mechanical events in a mechanical context, troubleshooting events in a technical troubleshooting context, electrical events, product design or production events, project events, collaboration events, etc.

At block 602, the event management system 102 obtains medical information corresponding to a user. For example, the event management system 102 can obtain medical information for a specific user to generate an event for the specific user based on the medical information corresponding to the specific user. The medical information may be obtained from the user, a storage, one or more client devices 120, and/or any other source.

At block 604, the event management system 102 generates an event based on the medical information. The event management system 102 can process the medical information to identify an event or action that is to be performed by the user, such as a prescribed task (e.g. consume medicine according to a defined schedule), a schedule or appointment (e.g., an appointment with a healthcare practitioner or medical test provider), a screening test, etc. As another example, an event may involve actions to be performed by the user (or with assistance of a caregiver), such as taking the user's weight (for CHF patients), measuring the user's blood sugar levels (diabetics), taking medicines, or performing exercises. In one embodiment, the action and/or event may be inferred by the event management system 102 by parsing the medical information. In yet another embodiment, the event may be associated with and/or otherwise connected to a physical location or a virtual location based upon a network-enabled container (e.g. a Bluetooth-enabled medication container of the user).

At block 606, the event management system 102 generates a code (e.g., encrypted code 206), such as an alphanumeric code, a barcode, or a QR code, which contains encoded data corresponding to the event and medical information. For example, referring to FIG. 1, the code generator 104 of the event management system 102 can automatically embed the event and/or medical information into an encrypted code (e.g., an alphanumeric code, a barcode, a QR code, etc.), as well as other additional information or executable data as previously explained with reference to FIGS. 1 and 2.

At block 608, the event management system 102 transmits the code to a client device $120_1$ associated with the user. After receiving the code, at block 610, the client device $120_1$ decodes the code to extract encoded data from the code. As previously explained, the encoded data can include event information, one or more parameters (e.g., triggering parameters, communications parameters, configuration parameters, rule parameters, etc.), executable code or instructions, other information for the user and/or event (e.g., user information, event-related information, background information, instructions, etc.), and so forth.

At block 612, based on the code, the client device $120_1$ and/or the executable data from the encoded code can configure the event on the client device $120_1$ and/or one or more client applications 130 on the client device $120_1$. For example, in some cases, executable code within the encoded data can, upon being executed by the client device $120_1$, configure the event in one or more client applications 130 at the client device $120_1$, such as a calendar application, a map or geolocation application, etc., including any parameters and/or information associated with the event defined in the code generated by the event management system 102. In some examples, the client device $120_1$ and/or a calendar application at the client device $120_1$ can inject the event and information from the encoded data into the calendar application, and configure one or more reminders or alerts for the event to be generated and communicated for the event. In some examples, the calendar reminder or alert may propose or configure a specific time, date, and/or range of times/dates for the event to be performed by the user and/or a person acting on behalf of the user associated with the event and client device $120_1$.

At block 614, the event management system 102 can receive an indication that the code has been received and/or processed by the client device $120_1$. For example, referring to FIG. 1, the event management system 102 may receive an indication that the code has been inputted, captured or otherwise scanned, and decoded at the client device $120_1$. As explained in block 612, as a result of the capture or scanning and decoding of the code, the client device $120_1$ can configure the event at the client device $120_1$ (e.g., at one or more client applications 130). For example, a calendar application 130 at the client device $120_1$ can be auto-populated with an event and a calendar reminder indication, based on the event and/or data (e.g., user information, event information, parameters, executable code, preferences, etc.) embedded within the inputted or scanned code. At block 616, the event management system 102 can monitor the event configured at the client device $120_1$. For example, the event management system 102 can monitor a calendar reminder indication to determine whether input to the client device $120_1$ or actions associated with the client device $120_1$ are indicative of compliance with the event or indicative of non-compliance with the event. In some cases, the event management system 102 can monitor the event based on event configuration information available to the event management system 102 and/or activity or communications from the client device $120_1$. For example, the event management system 102 can receive notifications from the client device $120_1$ when the event occurs, lapses, fails, etc., and/or can request updates from the client device $120_1$ regarding the event.

At block 618, the client device $120_1$ or event management system 102 can generate an action (e.g., a reminder, a notification, a report, a log, an output, a request, an electronic message, an alert, etc.) associated with the event based on a triggering condition (e.g., one or more triggers defined by rules and/or parameters from the encoded data)

associated with the event. In some cases, the action can be generated at least in part based on the monitoring of the event in block 616. For example, the action can be generated based on monitoring or detection of an occurrence of the event and/or one or more triggers for the action associated with the event.

In one example, a calendar application at the client device $120_1$ having the event configured based on the code can trigger an alert, reminder, task, or electronic message associated with the event based on a date/time (or range of dates/times), a location(s), a preference, a current state, a current condition, a current activity, etc., defined as a trigger for the event based on one or more parameters (e.g., rules, settings, conditions, instructions, etc.) configured for the event. To illustrate, the calendar application can generate a reminder that a conference (e.g., an event) is scheduled to start in 15 minutes or an alert that the conference has started or is scheduled to start.

In another example, a logging application at the client device $120_1$ can generate a notification or alert indicating that a computing error or condition has reached a triggering threshold and instructions for addressing the error or condition. In some configurations, the data from the code can be used to not only auto-configure the logging event by the logging application and the notification/alert, but also configure a troubleshooting operation such as a data or hardware scan, a computer restart, a reconfiguration of one or more settings associated with the error or condition, etc. In this way, the code can be implemented to not only configure and track time-sensitive, important, or distributed events; but also automatically identify and/or report time-sensitive or important event information; automatically troubleshoot such time-sensitive, important, or distributed events; etc.

In some cases, the action can include generating a call to an application service or device (e.g., API call) to provide information associated with the event (e.g., report a status associated with the event such as completed, incomplete, pending, canceled, etc.), request information associated with the event, prompt for a response or action for the event, process an operation or task associated with the event (e.g., a troubleshooting task, a refill of a prescription, a screening test, etc.), report a status of the client device $120_1$, etc.

Generating an action at block 618 can include transmitting an electronic message, such as a reminder or notification, to a display component, service and/or graphical interface at the client device $120_1$ so the electronic message is displayed or presented at the client device $120_1$ for the user. For example, the action can include generating and displaying a reminder on a display at the client device $120_1$ or any display device associated with the user. The reminder can be configured based on the code, including event data and/or parameters, and can include information configured for the reminder based on the code.

At block 620, the client device $120_1$ can transmit a network message (e.g., electronic message, network alert, etc.) to one or more devices (e.g., event management system 102, a second client device associated with the user, a client device associated with another user or entity such as a company or health care provider, etc.) based on the action and/or event. For example, the client device $120_1$ can send to the event management system 102 a notification indicating that the action or event has been triggered and/or has occurred or a reminder prompting the event management system 102 to generate additional events, reminders, notifications, tasks, etc. The client device $120_1$ can transmit a network message to the event management system 102 reporting the action and/or event, allowing the event management system 102 to track or monitor the event and/or associated actions (e.g., via the tracking service 110), and analyze patterns, events, event results, etc., which the event management system 102 can use to configure or adjust subsequent events for the client device $120_1$, the user associated with the client device $120_1$, and/or any other client devices 120 or users.

In some cases, the client device $120_1$ can transmit the network message to a network address associated with a particular destination, such as the event management system 102, defined for the network message. The network address can be determined based on one or more parameters included in the code, which including network addressing information and/or instructions for transmitting the network message or establishing a communication channel to deliver the network message to the particular destination.

In some configurations, the network message can be encrypted via one or more encryption schemes/algorithms (e.g., symmetric key/private key schemes, public key schemes, etc.) for security purposes. For example, the device $120_1$ can encrypt the network message via an encryption scheme/algorithm and transmit the network message to the destination in encrypted form. The recipient of the encrypted network message (e.g., the event management system 102) can receive the encrypted network message and decrypt it to obtain the plaintext message using one or more keys and/or algorithms depending on the particular encryption scheme/algorithm used to encrypt the network message. Moreover, in some cases, the recipient of the network message can perform a cyclic redundancy check or checksum to verify the authenticity of the received network message, detect errors in the received network message, check the overall data integrity of the network message, etc.

FIG. 7 illustrates an example method 700 for processing an encrypted code (e.g., 206), configuring an event (e.g., 212) encoded in the encrypted code, and performing an action associated with the event upon detecting a trigger defined for the event. The method 700 is described with respect to steps or blocks 702-712 performed by the client device $120_1$ as part of receiving and processing the code distributed in method 600 of FIG. 6. The method 700 can be part of method 600 or separate of method 600. For example, the method 700 can represent a sub-method, sub-steps, and/or sub-routines associated with the method 600 in FIG. 6, or a separate method, steps, routines, etc. Moreover, the method 700 is described with reference to client device $120_1$ performing the steps 702-712. However, in some configurations, one or more of the steps 702-712 can be performed by the event management system 102 or any other device associated with the event or code in the method.

At block 702, the client device $120_1$ can receive a code (e.g., encrypted code 206) from a particular source, such as event management system 102 or another system, which has been embedded with data for configuring an event on the client device $120_1$. At block 704, the client device $120_1$ can decode the received code to extract data embedded in the code. The client device $120_1$ can decode the received code via a decoder service 134 (e.g., a decoder tool, engine, application, etc.), as described with reference to FIG. 1.

At block 706, the client device $120_1$ can configure the event associated with the code based on the data extracted from the code when decoding the code. Configuring the event can include scheduling an action or activity, such as a reminder, alert or notification; inputting information about the event, such as descriptive information, background information, reference information, links, etc.; configuring parameters for the event, such as preferences, settings, outputs, triggers, rules, conditions, exceptions, operations, formatting instructions, etc.; configuring one or more applications 130 and/or resources at the client device 120₁ to perform actions, tasks, or operations associated with the event, such as monitoring event conditions or parameters, monitoring client device conditions (e.g., activity, location, movement, status, etc.), sensing information or collecting measurements, etc. For example, configuring the event can include injecting the event and related rules into a calendar application, providing monitoring or measuring instructions for a geolocator service, providing timing information to a time service, configuring tasks or operations by one or more specific applications, services, and/or resources on the client device 120₁, etc.

At block 708, the client device 120₁ can monitor the event and associated trigger(s) to determine at block 710 whether a triggering condition(s) for the event has occurred or has been satisfied. If the client device 120₁ can determines that a triggering condition(s) has not occurred or has not been satisfied at block 710, the method 700 returns to block 708 where the client device 120₁ monitors the event and associated trigger(s). If the client device 120₁ detects that the triggering condition(s) has occurred or has been satisfied at block 710, the client device 120₁ can proceed to block 712 where the client device 120₁ can perform an action associated with the configured event. The action can involve an electronic message, such as a reminder, notification, or alert; an application output; a user or device prompt; a particular operation such as launching an application, accessing a resource, troubleshooting an issue, initiating a procedure, stopping a service (e.g., a computing service, a subscription service, etc.), transmitting a request, delivering a response or data, generating application calls (e.g., API calls) to trigger a software function or service (e.g., a cloud-hosted function), etc.

In some cases, the action can involve presenting a reminder or notification in a display for the user, and/or pertinent information for the user. In addition, the action can involve transmitting additional communications (e.g., reminders or notifications) to remote devices, such as the event management system 102, a remote server, a database system, a user device, etc. In some cases, the client device 120₁ can encrypt the communications transmitted to the remote device(s) as previously explained. For example, the client device 120₁ can send an encrypted reminder or notification to a remote device, such as the event management system 102, to protect or secure the information being transmitted. If the action involves presenting a reminder or notification (or other information) in a display for the user, in some cases, the user may be required to first input a code or password to verify the user's identity for security purposes, prior to presenting such information on the display.

Figure 8:
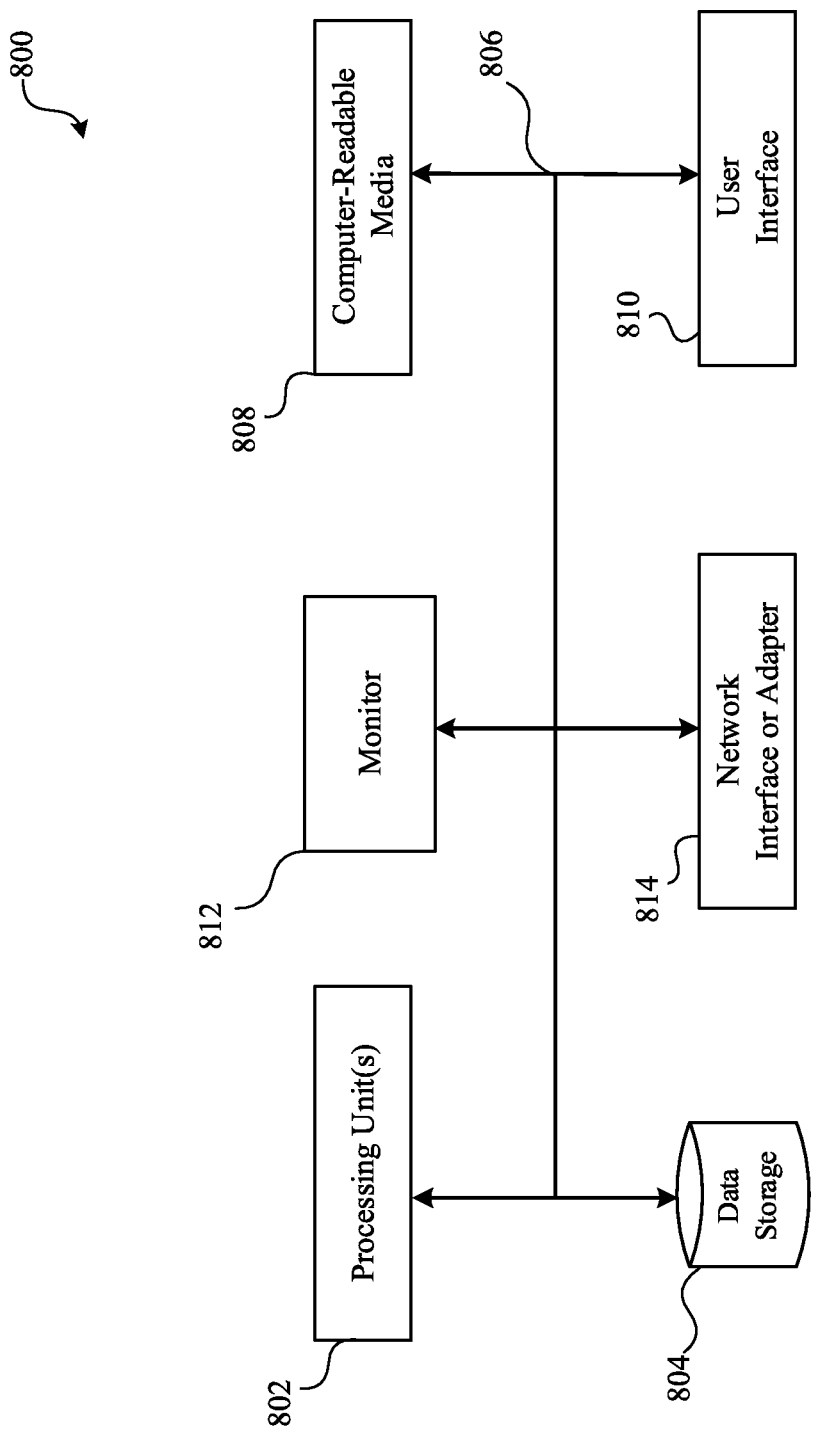
FIG. 8 is a block diagram illustrating an example device for processing an encrypted code and configuring events and associated actions based on encoded data in the encrypted code, according to aspects of the present disclosure.

The disclosure now turns to FIG. 8 which illustrates an example computing device architecture 800 for a computing device, such as event management system 102 or client device 120₁, suitable for performing computing steps and operations and implementing various aspects of the present disclosure. As illustrated, the computing device architecture 800 includes a general purpose computing device, although it is contemplated that the computing device architecture 800 may include one or more other computing systems, such as personal computers, server computers, hand-held or laptop devices, tablet devices, multiprocessor systems, IoT devices, set-top boxes, programmable consumer electronic devices, network devices, minicomputers, mainframe computers, digital signal processors, state machines, logic circuitries, distributed computing environments or infrastructure that include any of the above computing systems or devices, smart devices (e.g., smart wearable devices, smart televisions, etc.), and the like.

Components of the computer 800 may include various hardware components, such as a processing unit 802, a data storage 804 (e.g., a system memory), and a system bus 806 that couples various system components of the computer 800 to the processing unit 802. The system bus 806 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 800 may further include a variety of computer-readable media 808 that includes removable/non-removable media and volatile/nonvolatile media, but excludes transitory propagated signals. Computer-readable media 808 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 800. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 804 includes computer storage media in the form of volatile/nonvolatile memory such as read only memory (ROM) and random access memory (RAM). A basic input/output system (BIOS), containing the basic routines that help to transfer information between elements within the computer 800 (e.g., during start-up) is typically stored in ROM. RAM typically contains data and/or program modules that are immediately accessible to and/or presently being operated on by processing unit 802. For example, in one embodiment, data storage 804 holds an operating system, application programs, and other program modules and program data.

Data storage 804 may also include other removable/non-removable, volatile/nonvolatile computer storage media. For example, data storage 804 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 8, provide storage of computer-readable instructions, data structures, program modules and other data for the computer 800.

A user may enter commands and information through a user interface 810 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 802 through a user interface 810 that is coupled to the system bus 806, but may be connected by other interface and bus structures, such as a parallel port, game port or a universal serial bus (USB). A monitor 812 or other type of display device is also connected to the system bus 806 via an interface, such as a video interface. The monitor 812 may also be integrated with a touch-screen panel or the like.

The computer 800 may operate in a networked or cloud-computing environment using logical connections of a network interface or adapter 814 to one or more remote devices, such as a remote computer. The remote computer may be a personal computer, a server, a router, a network PC, a peer device or other common network node, and typically includes many or all of the elements described above relative to the computer 800. The logical connections depicted in FIG. 8 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 800 may be connected to a public and/or private network through the network interface or adapter 814. In such embodiments, a modem or other means for establishing communications over the network is connected to the system bus 806 via the network interface or adapter 814 or other appropriate mechanism. A wireless networking component including an interface and antenna may be coupled through a suitable device such as an access point or peer computer to a network. In a networked environment, program modules depicted relative to the computer 800, or portions thereof, may be stored in the remote memory storage device.

The foregoing illustrates the principles of the disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

Claim language reciting "at least one of" refers to at least one of a set and indicates that one member of the set or multiple members of the set satisfy the claim. For example, claim language reciting "at least one of A and B" means A, B, or A and B.

What is claimed is:

1. A method for distributing encrypted codes over a network to client devices, the method comprising:
   obtaining, by an event management system, respective information corresponding to a user associated with a set of users or devices;
   generating, by the event management system, a user-specific event based on the respective information, the user-specific event comprising a respective action determined based on the respective information and one or more triggers for performing the respective action;
   generating, by the event management system, an encrypted scannable code with encoded data corresponding to the user-specific event and the respective information, wherein the encoded data of the encrypted scannable code includes:
      executable data for deploying the user-specific event in one or more client applications associated with the user; and
      auto-configuration parameters for auto-configuring the user-specific event after the user-specific event is deployed in the one or more client applications;
   transmitting, by the event management system, over a network, the encrypted scannable code to a respective client device associated with the user, wherein scanning the encrypted scannable code causes the respective client device to:
      obtain the executable data for deploying the user-specific event by decoding the encrypted scannable code;
      deploy the user-specific event in a respective client application on the respective client device, wherein deploying the user-specific event comprises injecting the executable data of the encrypted scannable code in the respective client application;
      obtain the auto-configuration parameters based on decoding the encrypted scannable code;
      auto-configure the deployed user-specific event in the respective client application using the auto-configuration parameters of the encrypted scannable code; and
      trigger the one or more triggers to activate the respective client application to perform the respective action associated with the user-specific event, the respective action comprising transmitting, to the event management system or a display associated with the respective client device, an electronic message indicating a status of at least one of the user-specific event or the respective action associated with the user-specific event; and
   receiving an indication that the event has occurred or the one or more triggers have been satisfied.

2. The method of claim 1, wherein the electronic message comprises at least one of an alert or a reminder, and wherein the respective action further comprises generating the at least one of the alert or the reminder.

3. The method of claim 1, wherein the status of at least one of the user-specific event or the respective action associated with the user-specific event comprises at least one of a pending status, a completed status, a canceled status, or a start status.

4. The method of claim 1, wherein the executable data and the auto-configuration parameters in the encoded data of the encrypted scannable code, when decoded and processed at the respective client device, further cause the respective client application or the respective client device to monitor the one or more triggers based on at least one of a status associated with the respective client device, a location service associated with the respective client device, or a time service associated with the respective client device.

5. The method of claim 4, wherein the one or more triggers define one or more conditions, the one or more conditions comprising at least one of a time, a location, a precursor event, or a detected activity.

6. The method of claim 1, wherein:
the encoded data of the encrypted scannable code further includes network addressing information for communicating event-related information between the event management system and the respective client device over the network; and
the indication comprises an electronic communication transmitted over the network based on the network addressing information.

7. The method of claim 6, wherein the electronic communication associated with the indication comprises at least one of an alert, a notification, or a reminder.

8. The method of claim 1, wherein the encrypted scannable code comprises at least one of an alphanumeric code, a QR code, a barcode, or a graphical pattern.

9. The method of claim 1, wherein:
the respective client application comprises a calendar application;
the respective information comprises medical information corresponding to the user; and
the user-specific event comprises a medical event, the medical event comprising at least one of a treatment, a test, or a medical task.

10. The method of claim 1, wherein the executable data and the auto-configuration parameters in the encoded data of the encrypted scannable code, when decoded and processed at the respective client device, cause the user-specific event and the auto-configuration parameters to be auto-configured in the respective client application according to one or more formats or constraints associated with the respective client application, the one or more formats or constraints being defined by at least one of the executable data and the auto-configuration parameters.

11. The method of claim 1, wherein the respective action associated with the user-specific event comprises an application programming interface call to a remote application, the call requesting execution of one or more functions by the remote application, the one or more functions being associated with the user-specific event.

12. A system for distributing encrypted codes over a network to client devices, the system comprising:
one or more processors; and
at least one computer-readable medium storing instructions which, when executed by the one or more processors, cause the system to:
obtain respective information corresponding to a user associated with a set of users or devices;
generate a user-specific event based on the respective information, the user-specific event comprising a respective action determined based on the respective information and one or more triggers for performing the respective action;
generate an encrypted scannable code with encoded data corresponding to the user-specific event and the respective information, wherein the encoded data of the encrypted scannable code includes executable data for deploying the user-specific event in one or more client applications associated with the user and auto-configuration parameters for auto-configuring the user-specific event after the user-specific event is deployed in the one or more client applications;
transmit, over a network, the encrypted scannable code to a respective client device associated with the user, wherein scanning the encrypted scannable code causes the respective client device to:
obtain the executable data for deploying the user-specific event by decoding the encrypted scannable code;
deploy the user-specific event in a respective client application on the respective client device, wherein deploying the user-specific event comprises injecting the executable data of the encrypted scannable code in the respective client application;
obtain the auto-configuration parameters based on decoding the encrypted scannable code;
auto-configure the deployed user-specific event in the respective client application using the auto-configuration parameters of the encrypted scannable code; and
trigger the one or more triggers to activate the respective client application to perform the respective action associated with the user-specific event, the respective action comprising transmitting, to the event management system or a display associated with the respective client device, an electronic message indicating a status of at least one of the user-specific event or the respective action associated with the user-specific event; and
receive an indication that the event has occurred or the one or more triggers have been satisfied.

13. The system of claim 12, wherein the electronic message comprises at least one of an alert or a reminder, and wherein the status of at least one of the user-specific event or the respective action associated with the user-specific event comprises at least one of a pending status, a completed status, a canceled status, or a start status.

14. The system of claim 12, wherein the executable data and the auto-configuration parameters in the encoded data of the encrypted scannable code, when decoded and processed at the respective client device, further cause the respective client application or the respective client device to monitor the one or more triggers based on at least one of a status associated with the respective client device, a location service associated with the respective client device, or a time service associated with the respective client device.

15. The system of claim 14, wherein the one or more triggers define one or more conditions, the one or more conditions comprising at least one of a time, a location, a precursor event, or a detected activity.

16. The system of claim 12, wherein the encoded data of the encrypted scannable code further includes network addressing information for communicating event-related information between an event management system and the respective client device over the network, and wherein the indication comprises an electronic communication transmitted over the network based on the network addressing information, the electronic communication comprising at least one of an alert, a notification, or a reminder.

17. A non-transitory computer-readable storage medium comprising:

instructions stored thereon which, when executed by one or more processors, cause the one or more processors to:
  obtain respective information corresponding to a user associated with a set of users or devices;
  generate a user-specific event based on the respective information, the user-specific event comprising a respective action determined based on the respective information and one or more triggers for performing the respective action;
  generate an encrypted scannable code with encoded data corresponding to the user-specific event and the respective information, wherein the encoded data of the encrypted scannable code includes executable data for deploying the user-specific event in one or more client applications associated with the user and auto-configuration parameters for auto-configuring the user-specific event after the user-specific event is deployed in the one or more client applications;
  transmit, over a network, the encrypted scannable code to a respective client device associated with the user, wherein scanning the encrypted scannable code causes the respective client device to:
    obtain the executable data for deploying the user-specific event by decoding the encrypted scannable code;
    deploy the user-specific event in a respective client application on the respective client device, wherein deploying the user-specific event comprises injecting the executable data of the encrypted scannable code in the respective client application;
    obtain the auto-configuration parameters based on decoding the encrypted scannable code;
    auto-configure the deployed user-specific event in the respective client application using the auto-configuration parameters of the encrypted scannable code; and
    trigger the one or more triggers to activate the respective client application to perform the respective action associated with the user-specific event, the respective action comprising transmitting, to the event management system or a display associated with the respective client device, an electronic message indicating a status of at least one of the user-specific event or the respective action associated with the user-specific event; and
  receive an indication that the event has occurred or the one or more triggers have been satisfied.

18. The non-transitory computer-readable storage medium of claim 17, wherein the respective action associated with the user-specific event comprises an application programming interface call to a remote application, the call requesting execution of one or more functions by the remote application, the one or more functions being associated with the user-specific event.

19. The non-transitory computer-readable storage medium of claim 17, wherein the executable data and the auto-configuration parameters in the encoded data of the encrypted scannable code, when decoded and processed at the respective client device, further cause the respective client application or the respective client device to monitor one or more conditions associated with the one or more triggers, the one or more conditions comprising at least one of a time, a location, a precursor event, a condition detected via a sensor device, or a detected activity.

20. The non-transitory computer-readable storage medium of claim 17, wherein the respective client application comprises a calendar application, wherein the respective information comprises medical information corresponding to the user, and wherein the user-specific event comprises a medical event, the medical event comprising at least one of a treatment, a test, or a medical task.

* * * * *